United States Patent
Anderson et al.

(10) Patent No.: US 11,348,665 B2
(45) Date of Patent: May 31, 2022

(54) DIAGNOSING AND TREATING NEUROLOGICAL IMPAIRMENTS

(71) Applicant: International Business Machines Corporation, Armonk, NY (US)

(72) Inventors: Ryan R. Anderson, Kensington, CA (US); Joseph Kozhaya, Morrisville, NC (US)

(73) Assignee: International Business Machines Corporation, Armonk, NY (US)

( * ) Notice: Subject to any disclaimer, the term of this patent is extended or adjusted under 35 U.S.C. 154(b) by 564 days.

(21) Appl. No.: 16/184,455

(22) Filed: Nov. 8, 2018

(65) Prior Publication Data

US 2020/0152296 A1 May 14, 2020

(51) Int. Cl.
| | |
|---|---|
| *G16H 10/20* | (2018.01) |
| *G16H 50/20* | (2018.01) |
| *G16H 20/70* | (2018.01) |
| *G06N 3/04* | (2006.01) |
| *G06N 3/063* | (2006.01) |
| *G16H 20/10* | (2018.01) |
| *G16H 20/40* | (2018.01) |

(52) U.S. Cl.
CPC .............. *G16H 10/20* (2018.01); *G06N 3/04* (2013.01); *G06N 3/063* (2013.01); *G16H 20/70* (2018.01); *G16H 50/20* (2018.01); *G16H 20/10* (2018.01); *G16H 20/40* (2018.01)

(58) Field of Classification Search
CPC ............................ A61B 5/4064; G16H 50/20
See application file for complete search history.

(56) References Cited

U.S. PATENT DOCUMENTS

| | | | |
|---|---|---|---|
| 6,221,908 B1 | 4/2001 | Kilgard et al. | |
| 10,002,130 B1 | 6/2018 | Thomas et al. | |
| 2004/0009549 A1* | 1/2004 | Grigoriev | A61P 9/12 435/325 |
| 2015/0335288 A1* | 11/2015 | Toth | A61B 5/6833 600/391 |
| 2016/0113567 A1* | 4/2016 | Osvath | A61B 5/291 600/544 |
| 2016/0117940 A1 | 4/2016 | Gomory et al. | |
| 2016/0267809 A1 | 9/2016 | Decharms et al. | |
| 2016/0354061 A1 | 12/2016 | Hecker et al. | |
| 2017/0200075 A1 | 7/2017 | Suskind et al. | |
| 2017/0250930 A1 | 8/2017 | Ben-Itzhack | |

(Continued)

OTHER PUBLICATIONS

P. Mell et al., "The NIST Definition of Cloud Computing", National Institute of Standards and Technology, Information Technology Laboratory, Sep. 2011, pp. 1-7.

(Continued)

*Primary Examiner* — Reginald R Reyes
(74) *Attorney, Agent, or Firm* — Law Office of Jim Boice

(57) ABSTRACT

A method administers a therapeutic treatment for a neurological impairment of a patient. One or more processor(s) display query content on a display, and then receive responses to the query content from a patient. The processor(s) identify a physiological locus of a neurological impairment of the patient based on the responses to the query content from the patient, and administer a therapeutic treatment to the patient based on the identified physiological locus of the neurological impairment of the patient.

18 Claims, 11 Drawing Sheets

(56) References Cited

U.S. PATENT DOCUMENTS

2019/0001117 A1\* 1/2019 Ben-David .......... A61B 5/0205
2019/0034564 A1\* 1/2019 Narcross ................ G06N 3/049

OTHER PUBLICATIONS

American Association for the Advancement of Science. "A personalized rehabilitation algorithm helps stroke patients walk again." ScienceDaily. ScienceDaily, Jul. 19, 2017. <www.sciencedaily.com/releases/2017/07/170719140942.htm>, pp. 1-2.
L. J. Volz et al., "Shaping Early Reorganization of Neural Networks Promotes Motor Function After Stroke", Oxford University Press, Cerebral Cortex, Jun. 2016, 26, pp. 2882-2894.
E. Lee et al., "Deep Into the Brain: Artificial Intelligence in Stroke Imaging", 2017, Korean Stroke Society, Journal of Stroke 19(3), pp. 277-285.
Harvard Women's Health Watch, "Could a Silent Stroke Erode Your Memory?" Jun. 2012, Harvard Health Publishing, Harvard Medical School, pp. 1-3.
Flint Rehab, "28 Stroke Recovery Tips for Healing, Habits, and Happiness", 2016, www.flintrehab.com, pp. 1-21.
Flint Rehab, "What You Should Do Every Morning To Boost Stroke Recovery", 2016, www.flintrehab.com, pp. 1-8.
National Institute of Health, "NIH Stroke Scale International", Retrieved Nov. 8, 2018, <http://www.nihstrokescale.org/>, pp. 1-2.

\* cited by examiner

DIAGNOSING AND TREATING NEUROLOGICAL IMPAIRMENTS

BACKGROUND

The present invention relates to the field of treating neurological impairments. Still more specifically, the present invention relates to the field of diagnosing physiological loci of neurological impairments in patients, and administering appropriate therapeutic treatments to the patients.

SUMMARY

In an embodiment of the present invention, a method administers a therapeutic treatment for a neurological impairment of a patient. One or more processor(s) display query content on a display, and then receive responses to the query content from a patient. The processor(s) identify a physiological locus of a neurological impairment of the patient based on the responses to the query content from the patient, and administer a therapeutic treatment to the patient based on the identified physiological locus of the neurological impairment of the patient.

In one or more embodiments, the method(s) described herein are performed by an execution of a computer program product and/or a computer system.

DETAILED DESCRIPTION

Figure 1:
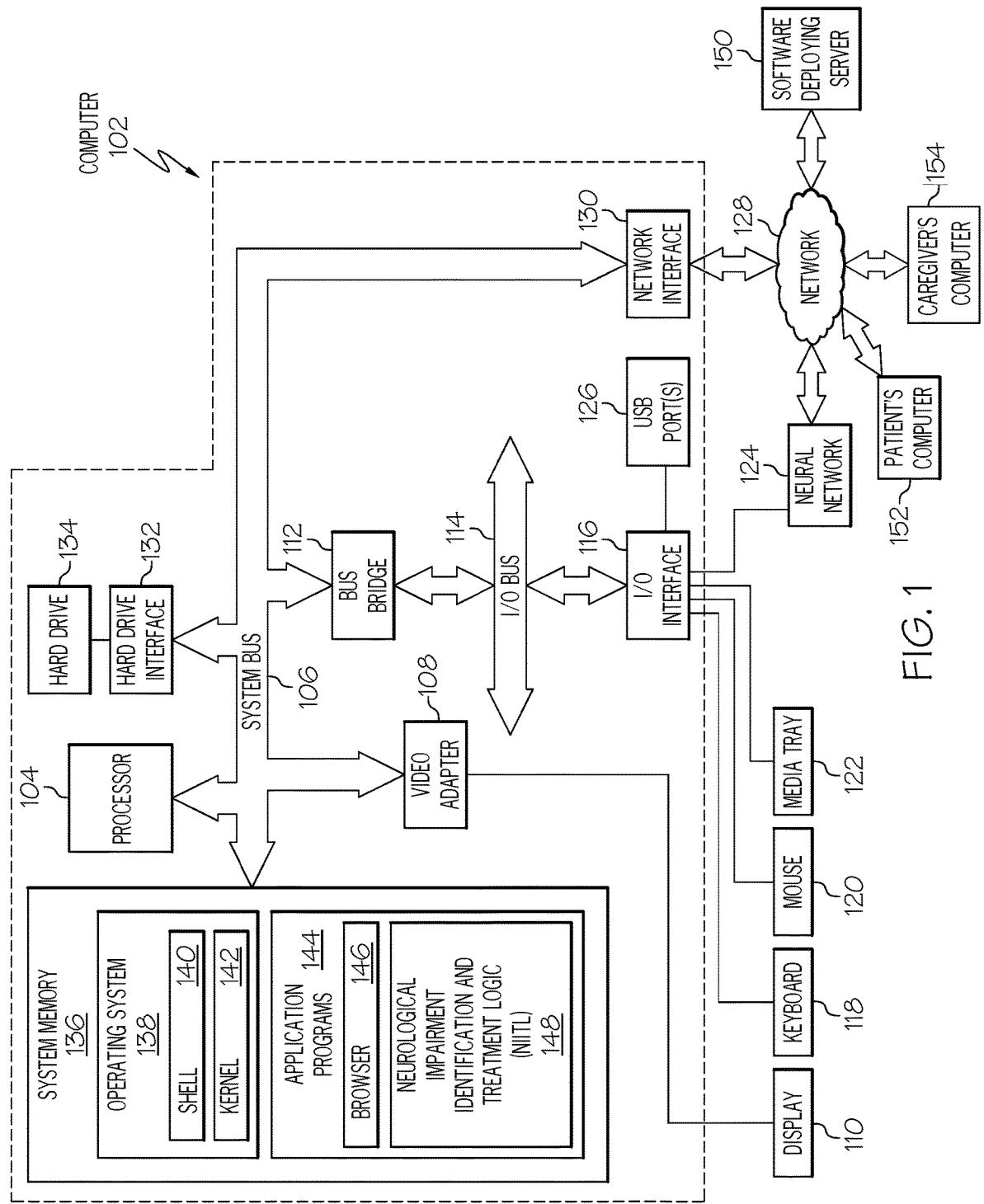
FIG. 1 depicts an exemplary system and network in which the present invention may be implemented.

In one or more embodiments, the present invention is a system, a method, and/or a computer program product at any possible technical detail level of integration. In one or more embodiments, the computer program product includes a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

In one or more embodiments, computer readable program instructions for carrying out operations of the present invention comprise assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. In one or more embodiments, the computer readable program instructions execute entirely on the user's computer, partly on the user's computer, as a stand-alone software package, partly on the user's computer and partly on a remote computer or entirely on the remote computer or server. In the latter scenario and in one or more embodiments, the remote computer connected to the user's computer through any type of network, including a local area network (LAN) or a wide area network (WAN), or the connection is made to an external computer (for example, through the Internet using an Internet Service Provider). In some embodiments, electronic circuitry including, for example, programmable logic circuitry, field-programmable gate arrays (FPGA), or programmable logic arrays (PLA) execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

In one or more embodiments, these computer readable program instructions are provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In one or more embodiments, these computer readable program instructions are also be stored in a computer readable storage medium that, in one or more embodiments, direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

In one or more embodiments, the computer readable program instructions are also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams represents a module, segment, or portion of instructions, which comprises one or more executable instructions for implementing the specified logical function(s). In some alternative implementations, the functions noted in the block occur out of the order noted in the figures. For example, two blocks shown in succession are, in fact, executed substantially concurrently, or the blocks are sometimes executed in the reverse order, depending upon the functionality involved. It will also be noted that, in one or more embodiments of the present invention, each block of the block diagrams and/or flowchart illustration, and combinations of blocks in the block diagrams and/or flowchart illustration, are implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Note that some or all of the exemplary architecture, including both depicted hardware and software, shown for and within computer 102 may be utilized by software deploying server 150 and/or patient's computer 152 and/or caregiver's computer 154 and/or neural network 124.

Exemplary computer 102 includes a processor 104 that is coupled to a system bus 106. Processor 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a neural network 124, and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 and/or the patient's computer 152 and/or caregiver's computer 154 and/or the neural network 124 using a network interface 130 to a network 128. Network interface 130 is a hardware network interface, such as a network interface card (NIC), etc. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (as well as software deploying server 150's system memory) also include a Neurological Impairment Identification and Treatment Logic (NIITL) 148. NIITL 148 includes code for implementing the processes described below, including those described in FIGS. 2-9. In one embodiment, computer 102 is able to download NIITL 148 from software deploying server 150, including in an on-demand basis, wherein the code in NIITL 148 is not downloaded until needed for execution. Note further that, in one embodiment of the present invention, software deploying server 150 performs all of the functions associated with the present invention (including execution of NIITL 148), thus freeing computer 102 from having to use its own internal computing resources to execute NIITL 148.

Also connected to (or alternatively, as part of) computer 102 is a neural network 124. In exemplary embodiments of the present invention, neural network 124 is a traditional neural network (see FIG. 4), a convolutional neural network (see FIGS. 5-7), or another type of heuristic artificial intelligence.

Also connected to computer 102 is caregiver's computer 154, which is used by a health care provider for a patient described herein, a family member of the patient described herein, etc. Such healthcare providers, professional or familial, provide information used to diagnose the patient's neurological impairment as described herein, and/or to provide therapeutic stimuli (e.g., names of familial members) used to treat the patient's neurological impairment.

Note that the hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

When people suffer brain strokes or suffer traumatic brain injuries (TBIs), the degree of damage and impairment can be difficult to ascertain. As such, one or more embodiments of the present invention help stroke and TBI patients with their recoveries by mapping the cognitive damage and tailoring the administration of therapeutic treatments accordingly.

One or more embodiments focus on diagnosing and treating minor ischemic strokes, in which a blood vessel in/to the brain is blocked. However, imaging diagnostic tools (e.g., magnetic resonance imaging—MRI) often return negative results (showing no evidence of a stroke), particular if the blockage is minimal. As such, these imaging diagnostic tools do not clearly identify where the vascular blockage is occurring within the brain.

Thus, one or more embodiments of the present invention utilize natural language interactions with the patient, caregivers and families, thus allowing the caregivers to identify damaged parts of the patient's own "knowledge graph" and cognitive functions.

One or more embodiments of the present invention map and classify the neurologic impairments, according to their nature (e.g., a vascular blockage), degree (e.g., total or partial), and level of damage (e.g., damage to a particular part of the brain caused by the vascular blockage).

One or more embodiments of the present invention utilizes both (1) general knowledge and neurological degradation (e.g. unable to read/spell/write "tractor", or identify a giraffe from an image); and/or (2) patient-unique knowledge gaps (e.g. the patient's nephew's name is "Billy").

One or more embodiments of the present invention utilize a cluster type of damage (e.g., using data from other patients and known outcomes), which enables: (a) recommendations for optimal recovery methods, therapies—using a predictive model and prior knowledge; and (b) conversational systems to probe into areas of greatest concern.

As such, one or more embodiments of the present invention supports the patient's recovery by: (a) supporting the creation of alternative neurological pathways (e.g., more conversations, stimulation of more workarounds, more reconnections) during recovery and rehabilitation; and (b) being an automated system that is available 24/7 with invariably consistent support and a regimen structured around encouraging repetitive tasks with positive feedback and an appropriate pace as determined by the system and/or the patient's caregiver.

One or more embodiments of the present invention utilizes visualizations (e.g., graphs) that: (a) improve neuroplasticity in the patient's brain; (b) leverage spatial components of the brain to provide alternate paths; (c) provide positive reinforcement and control of recovery, encouraging adherence to rehab; and (d) enable medical personnel to "see" gaps and progress in the patient's recovery.

Thus, one or more embodiments of the present invention address the problem of handling a situation in which a stroke and/or TBI has occurred, but the location, nature, and/or existence of the physical and neurological damage is unknown. One or more embodiments of the present invention map and measure the damage in order to diagnose the problem and formulate the appropriate therapy.

As such, one or more embodiments of the present invention use a conversational agent to map and better understand the nature of neurological damage to a patient's brain.

This conversational agent/mode encourages the neuroplastic brain in recovery by guiding the patient in finding alternate neural pathways, in order to repair the neurological damage. For example, if the patient forgot the name of his/her nephew, an embodiment of the present invention will present related information (e.g., an old story about fishing with the nephew), thus "jogging" an alternate path for the memory of the nephew's name.

Natural Language Understanding builds out a knowledge graph of the patient with each conversation by analyzing text that is generated by the system and responses provided by the patient. In an embodiment of the present invention, the system accepts doctor, therapist and/or family input for known gaps in the knowledge graph.

One or more embodiments of the present invention use explicit flagging of gaps (e.g., the patient stating, "I cannot read the newspaper anymore; but I used to be able to.").

One or more embodiments of the present invention provide a mechanism to differentiate between general knowledge gaps (e.g. failure to recall the word "giraffe" when shown an image) versus unique knowledge gaps (e.g., the name of the patient's nephew). In this embodiment, general knowledge may further be determined to match what is considered "general knowledge" for a population similar to the patient. That is, if the system determines that a general knowledge question falls outside the experience or knowledge of the patient, an alternate question may be supplied so that a patient's lack of response does not register as a "false positive" when determining what cognitive areas may be impaired.

One or more embodiments of the present invention provide a visualization of both "intact" and "damaged" cognitive areas by presenting spatial representations that allow the patient to visualize their own cognitive gaps, work around them, and see their progress.

One or more embodiments of the present invention leverage the patient's neuroplasticity, which is a neurological mechanism that allows the brain to develop alternative neural pathways in response to damage to another neural pathway in the brain.

As such, one or more embodiments of the present invention leverage a template-based conversational agent to help in the recovery of stroke patients. The template based approach allows the conversational agent to be trained on General Knowledge as well as Unique Knowledge to personalize the interaction with the patient for the purposes of identifying what parts of the brain are most impacted by the stroke as well as suggesting repetitive tasks to help speed up the patients' recovery.

As described herein, one or more embodiments of the present invention use templates that are leveraged by conversational agents (and/or conditional dialog flows) to personalize the healing process for stroke patients by first identifying damaged brain areas via conversational communications, and then by guiding/motivating repetitive activities to help with the brain's neuroplasticity.

In one or more embodiments of the present invention, a system and method improve stroke recovery via conversational agents which enable experts to upload general and personalized content in template format. In one or more embodiments of the present invention, these conversational agents are trained based on uploaded template-based information, leading to a triggering of communications between the conversational agents and the patient. The responses from the patient and other interactions between the conversational agents and the patient are then used to identify areas of brain damage. This leads to the system suggesting and administering repetitive mental activities to speed the recovery of damaged brain areas.

In one or more embodiments of the present invention, a person's knowledge is modeled as a collection of entities and relations. Some of these entities/relations are shared by a majority of a population, while others are unique to the person in regard to family, friends, and work environment. The shared knowledge is represented in a General Knowledge Graph, and the patient's unique knowledge is represented in a Personal Knowledge Graph.

When a person suffers a stroke, some of his/her knowledge is erased. One recommended approach to recovery is applying repetitive tasks to help the patient "remember" the knowledge he/she lost. In one or more embodiments of the present invention, a conversational agent is trained on both General Knowledge as well as Unique Knowledge of a patient. This conversational agent then communicates with the patient to identify what parts of the brain are most impacted and accordingly provides queues and hints to guide the patient to recovery.

This template-based approach allows doctors and family members to provide information based on various templates which the conversational agent leverages in order to personalize the experience with the patient. For instance, doctors/neuropsychologists provide general information (pictures of giraffes and horses, news information, history, geography, physics, math facts, etc.) that can help isolate what part of the brain is most impacted by the stroke. Family members then provide pictures of family members, family specific information from a variety of occasions, and personal information only known to the family members. Co-workers provides information specific to the patient's job role and work environment.

In one or more embodiments of the present invention, there are multiple conversational agents, each focused on evaluating a particular aspect of potential brain damage as well as providing recommended communications to address that brain damage. For instance, one conversational agent is focused on asking questions that relate to language skills; another one focused on asking questions related to facial recognition, and so on. A master conversational agent then orchestrates the dialog among the various individual agents.

In another embodiment of the present invention, there is only one conversational agent with multiple dialog branches that correspond to identifying various possible brain damage areas.

Figure 2:
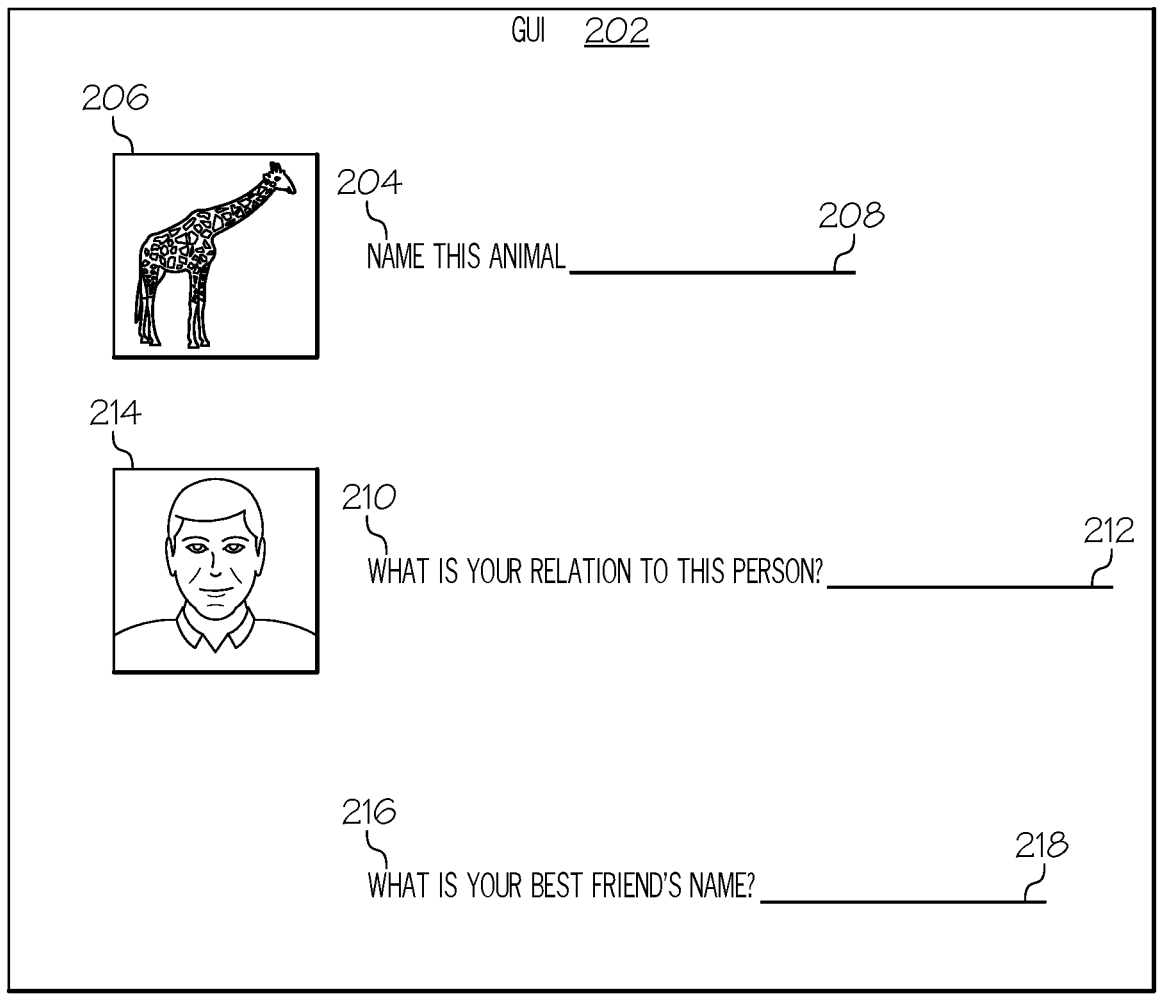
FIG. 2 illustrates a graphical user interface from which a patient answers cognitive questions in accordance with one or more embodiments of the present invention.

With reference now to FIG. 2, assume that one or more conversational agents (e.g., part of NIITL 148 shown in FIG. 1) have generated a GUI 202 on the patient's computer 152 shown in FIG. 1. GUI 202 presents several questions to the patient, including general knowledge questions (about information that most persons would know the answer to) and unique knowledge questions (about information that only the patient and a few other persons would know the answer to).

An example of a general knowledge question is shown in question 204, which asks the patient to enter (type, speak, etc.) the name of the animal (e.g., a giraffe) shown in picture 206 into active field 208, which is then returned to the conversational agent(s).

Examples of unique knowledge questions may be visually-based or textually-based. For example, an exemplary visually-based unique knowledge question shown in FIG. 2 has the conversational agent asking (query block 210) the patient to enter in active field 212 the relationship between the patient and the person shown in picture 214 (e.g., the person shown in picture 214 can be a grandson, a co-worker, etc.), which is returned to the conversational agent. An exemplary textually-based question is shown as question 216, in which the conversational agent directs the patient to give the name of his/her best friend in active field 218, which is then sent to the conversational agent.

While GUI 202 is depicted as presenting text questions, in one or more other embodiments of the present invention the questions presented in GUI 202, and/or the reiterative training based on the patient's responses to these questions, are in the form of audio questions, video prompts, etc.

That is, in one or more embodiments of the present invention, the patient is presented with text, audio, audio-visual, etc. content, which asks the patient for information that the patient should know, were it not for the patient's neurological impairment. Once this neurological impairment is ascertained, based on the patient's responses to these questions, then text and/or audio and/or audio-visual content that reiteratively presents the correct answer to the questions that the patient was unable to answer are presented to the patient until the patient is able to correctly answer the questions, due to the neuroplasticity and training of the patient's brain.

Figure 3:
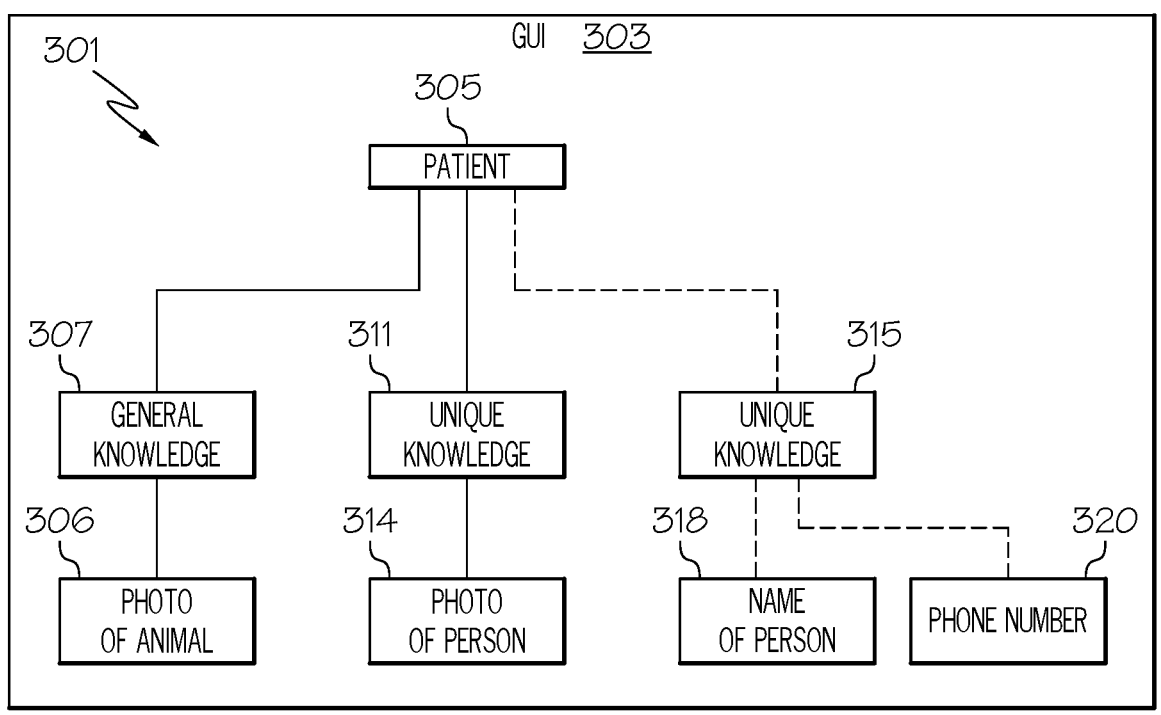
FIG. 3 depicts a graphical user interface that presents a relationship graph of a representation of a patient to representations of other entities in accordance with one or more embodiments of the present invention.

The responses from the patient to the questions in GUI 202 are then mapped into a relationship graph, such as the relationship graph 301 shown in GUI 303 in FIG. 3.

Assume now that in the GUI 202 shown in FIG. 2 that the patient correctly identified the animal in picture 206 as being a giraffe (thus having a good grasp of general knowledge information), and knows that the person shown in picture 214 is the patient's nephew (thus the patient is able to identify visually-based unique knowledge information).

However, assume further that the patient is unable to remember the name of his/her best friend, and thus is not able to recall textually-based unique knowledge. The three questions shown in FIG. 2 are for explanatory purposes, since a more complete evaluation of the cognitive ability of the patient uses many more questions, both visually-based and textually-based (and/or audio-based, etc.), in order to determine which cognitive abilities, if any, are affected and thus what part of the brain has been compromised.

As shown in relationship graph 301, since the patient has a good grasp of general knowledge, the node 305 for the patient is connected by a solid line (edge) to the box 307 that shows that the patient has a solid understanding that the photo of the animal shown in picture 206 in FIG. 2 is that of a giraffe (node 306 in FIG. 3). Similarly, since the patient is able to recognize photos of a person he/she knows, then the node 305 for the patient is connected by a solid line (edge) to the box 311 that shows that the patient recognizes a photo of a person that he/she knows shown in picture 214 in FIG. 2 (node 314 in FIG. 3). However, since the patient did not know the name of his/her best friend, then node 305 for the patient is connected by a dashed line (edge) to the box 315 that shows that the patient does not know the name of his/her best friend when he/she tries to give the name of his/her best friend in active field 218 in FIG. 2 (node 318 in FIG. 3).

Thus, in various embodiments of the present invention, relationship graph 301 shown in GUI 303 is presented to the health care provider(s) for the patient, the patient himself/herself, etc., in order to identify what types of cognitive abilities are impaired.

While the examples of information that the patient is trained to learn are shown in FIG. 3 as visual (e.g., node 306) and verbal (e.g., node 318), in other embodiments the information is audio (e.g., an audio recording) and/or audio-visual information (e.g., a video clip), which the patient is trained to view repeatedly until he/she is able to recognize.

In a preferred embodiment, as the cognitive abilities are improved, the connecting lines/edges transition from dashed (or otherwise visually encoded) to solid lines. This provides the health care provider with information about the progress of the patient, and gives the patient encouraging information as to how the therapy is working.

For example, assume that the patient is unable to remember the name of his best friend. In order to strengthen this knowledge (e.g., by generating alternate neural memory pathways in the patient's brain), the conversational agent will tell the patient the name of his/her best friend, and then prompt the patient to enter this name (immediately and then later, after the name is no longer fresh in the patient's mind) into the active field 218 shown in FIG. 2. Alternatively, the conversational agent will give the patient a mnemonic device to remember the name of his/her best friend, such as a letter code that is easy to remember, an anecdote that triggers the name of his/her best friend, etc.

In an embodiment of the present invention, once one issue is resolved, then the system will use other conversational agents to work on another problem. For example, assume that the conversational agent has received information from the patient via GUI 202 shown in FIG. 2 that the user is unable to remember his/her own phone number, as shown by the dashed line to node 320 in FIG. 3. In one embodiment of the present invention, the conversational agent waits until the patient has clearly demonstrated that he/she now remembers the name of his/her best friend (node 318) before training the patient how to use alternative neural pathways to remember his/her own phone number (node 320).

In another embodiment of the present invention, the conversational agent concurrently handles all cognitive impairments of a same type. For example, the conversational agent will provide different mnemonic devices to aid the patient in remembering various unique knowledge text-based information, including the name of his/her best friend (node 318) as well as his/her own phone number (node 320).

In one or more embodiments, the present invention uses an electronic neural network to model the patient's brain, in order to determine what type of neurological impairment is being experienced by the patient, and/or what part of the brain is being affected. That is, an electronic neural network not only has electronic neurons that map to various parts of the brain, but also emulates how the brain responds as a healthy brain as well as an impaired brain.

The neural network 124 shown in FIG. 1 is a Traditional Neural Network (TNN), a Convolutional Neural Network (CNN), or any other machine learning system. In a preferred embodiment, a TNN is used to evaluate text/numeric data, while a CNN is used to evaluate an image.

A neural network, as the name implies, is roughly modeled after a biological neural network (e.g., a human brain). A biological neural network is made up of a series of interconnected neurons, which affect one another. For example, a first neuron can be electrically connected by a synapse to a second neuron through the release of neurotransmitters (from the first neuron) which are received by the second neuron. These neurotransmitters can cause the second neuron to become excited or inhibited. A pattern of excited/inhibited interconnected neurons eventually lead to a biological result, including thoughts, muscle movement, memory retrieval, etc. While this description of a biological neural network is highly simplified, the high-level overview is that one or more biological neurons affect the operation of one or more other bio-electrically connected biological neurons.

An electronic neural network similarly is made up of electronic neurons. However, unlike biological neurons, electronic neurons are never technically "inhibitory", but are only "excitatory" to varying degrees.

In a TNN, neurons are arranged in layers, known as an input layer, hidden layer(s), and an output layer. The input layer includes neurons/nodes that take input data, and send it to a series of hidden layers of neurons, in which all neurons from one layer in the hidden layers are interconnected with all neurons in a next layer in the hidden layers. The final layer in the hidden layers then outputs a computational result to the output layer, which is often a single node for holding vector information.

Figure 4:
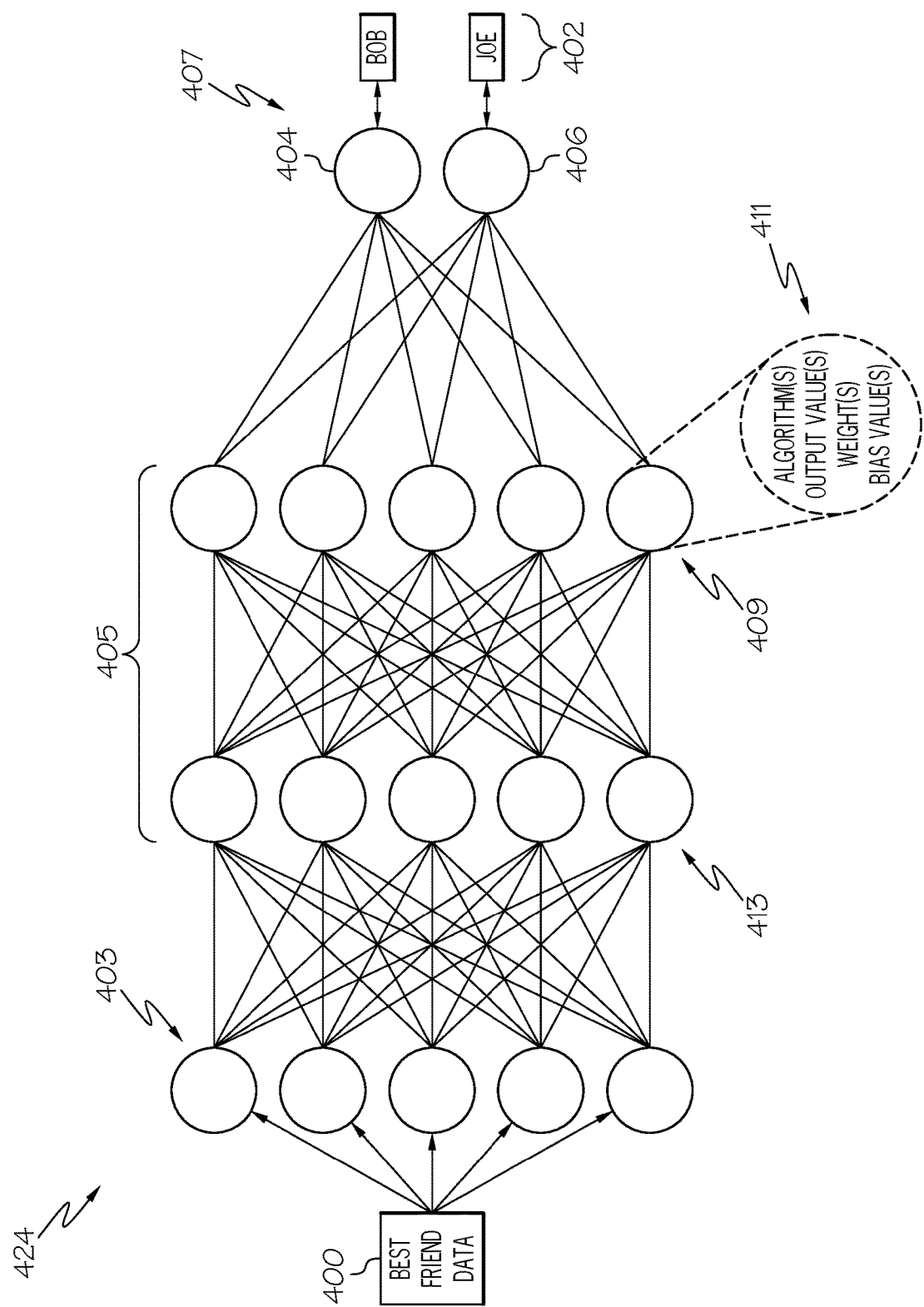
FIG. 4 depicts an exemplary traditional neural network as used in one or more embodiments of the present invention.

With reference now to FIG. 4, a Traditional Neural Network (TNN) 424 used to evaluate textual data in one or more embodiments of the present invention is presented. For example, best friend data 400 is text and/or data that describes features of a particular person, including his/her name, appearance, etc., that is the patient's best friend.

The electronic neurons in TNN 424 are arranged in layers, known as an input layer 403, hidden layers 405, and an output layer 407. The input layer 403 includes neurons/nodes that take input data, and send it to a series of hidden layers of neurons (e.g., hidden layers 405), in which neurons from one layer in the hidden layers are interconnected with all neurons in a next layer in the hidden layers 405. The final layer in the hidden layers 405 then outputs a computational result to the output layer 407, which is often a single node for holding vector information. In an embodiment of the present invention, each neuron in the output layer 407 is associated with a particular label from labels 402, as shown in FIG. 4.

As just mentioned, each node in the depicted TNN 424 represents an electronic neuron, such as the depicted neuron 409. As shown in block 411, each neuron (including neuron 409) functionally includes at least four features: an algorithm, an output value, a weight, and a bias value.

The algorithm is a mathematic formula for processing data from one or more upstream neurons. For example, assume that one or more of the neurons depicted in the middle hidden layers 405 send data values to neuron 409. Neuron 409 then processes these data values by executing the algorithm shown in block 411, in order to create one or more output values, which are then sent to another neuron, such as another neuron within the hidden layers 405 or a neuron in the output layer 407. Each neuron also has a weight that is specific for that neuron and/or for other connected neurons. Furthermore, the output value(s) are added to bias value(s), which increase or decrease the output value, allowing the TNN 424 to be further "fine tuned".

For example, assume that neuron 413 is sending the results of its analysis of a piece of data to neuron 409. Neuron 409 has a first weight that defines how important data coming specifically from neuron 413 is. If the data is important, then data coming from neuron 413 is weighted heavily, and/or increased by the bias value, thus causing the algorithm(s) within neuron 409 to generate a higher output, which will have a heavier impact on neurons in the output layer 407. Similarly, if neuron 413 has been determined to be significant to the operations of neuron 409, then the weight in neuron 413 will be increased, such that neuron 409 receives a higher value for the output of the algorithm in the neuron 413. Alternatively, the output of neuron 409 can be minimized by decreasing the weight and/or bias used to affect the output of neuron 409. These weights/biases are adjustable for one, some, or all of the neurons in the TNN 424, such that a reliable output will result from output layer 407. Such adjustments are alternatively performed manually or automatically.

When manually adjusted, the weights are adjusted by the user in a repeated manner until the output from output layer 407 matches expectations. For example, assume that input layer 403 receives inputs that describe the patient's best friend. In an exemplary input, the input to input layer 403 contains values that describe the best friend (e.g., his/her name, appearance, age, etc.). If TNN 424 has been properly trained (by adjusting the algorithm(s), output value(s), weight(s), and biases in one or more of the electronic neurons within TNN 424) to output a 5-tuple output vector (e.g., 0.9, 0.2) to the output layer 407, then it indicates that the neuron 404 that is associated with the label "Bob" has the highest value (0.9) (thus indicating that Bob is the patient's best friend). However, the TNN 424 is also trained to give a value of 0.2 to neuron 406, indicating that "Joe" is the incorrect label for the patient's best friend.

Assume now that each neuron in the hidden layers 405 is mapped to a particular locus (physical position) within the patient's brain. Assume further that a value of 0.99 is in neuron 406, indicating that the TNN 424 (incorrectly) "thinks" that the name of the best friend is Joe. As such, the electronic neurons within the hidden layers 405 are examined to determine which electronic neuron(s) are responsible for incorrectly causing the value 0.99 to populate neuron 406. That is, since the neurons in the TNN 424 are mapped to specific loci in the patient's brain, then an incorrect output to neuron 406 triggers an examination of the neurons within the hidden layers 405 to identify the physical loci in the patient's brain that is impaired.

When automatically adjusted, the weights (and/or algorithms) are adjusted using "back propagation", in which weight values of the neurons are adjusted by using a "gradient descent" method that determines which direction each weight value should be adjusted to. This gradient descent process moves the weight in each neuron in a certain direction until the output from output layer 407 improves (e.g., gets closer to outputting a highest value to neuron 404, thus indicating that the best friend data 400 is for "Bob"). That is, this automated "back propagation" is able to identify which specific electronic neurons (and thus the corresponding loci in the patient's brain) are impaired (i.e., have the wrong weights, bias, etc.).

A CNN is similar to a TNN in that both utilize interconnected electronic neurons. However, a CNN is different from a TNN in that 1) a CNN has neural layers whose sizes are based on filter sizes, stride values, padding values, etc. (see FIG. 6) and 2) a CNN utilizes a convolution scheme to analyze image data (see FIG. 7). A CNN gets its "convolutional" name based on a convolution (i.e., a mathematical operation on two functions to obtain a result) of filtering and pooling pixel data (a mathematical operation on two functions) in order to generate a predicted output (obtain a result).

Figure 5:
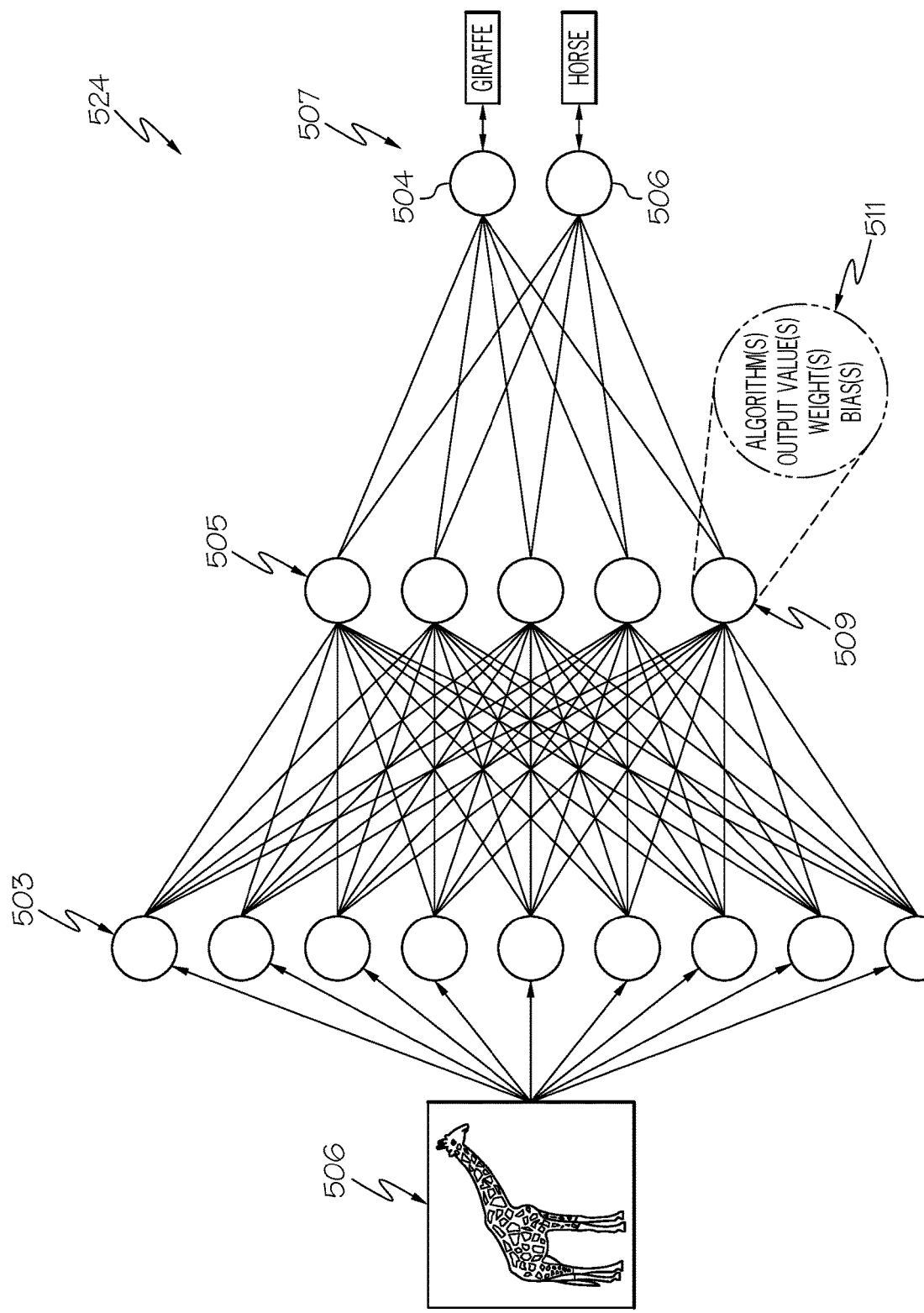
FIG. 5 illustrates an exemplary Convolutional Neural Network (CNN) as used in one or more embodiments of the present invention.

With reference now to FIG. 5, an exemplary CNN 524 is presented to model the patient's brain when evaluating a photo image. Each depicted node in FIG. 5 represents a neuron (i.e., an electronic neuron). In accordance with one or more embodiments of the present invention, an input layer 503 includes neurons that receive data that describes pixels from a photograph, such as animal image 506 (analogous to picture 206 shown in FIG. 2). The neurons from the input layer 503 of the CNN 524 connect neurons in a middle layer 505, which connect to neurons in the output layer 507.

As just mentioned, each node in the depicted CNN 524 represents an electronic neuron, such as the depicted neuron 509. As shown in block 511, each neuron (including neuron 509) functionally includes at least four features: an algorithm, an output value, a weight, and a bias (similar to those described in neuron nodes in the TNN 424 shown in FIG. 4).

For example, assume that neuron 513 is sending the results of its analysis of a piece of the animal image 501 to neuron 509. Neuron 509 has a first weight that defines how important data coming specifically from neuron 513 is. If the data is important, then data coming from neuron 513 is weighted heavily, thus causing the algorithm(s) within neuron 509 to generate a higher output, which will have a heavier impact on neurons in the output layer 507. Similarly, if neuron 513 has been determined to be significant to the operations of neuron 509, then the weight in neuron 513 will be increased, such that neuron 509 receives a higher value for the output of the algorithm in the neuron 513. These weights are adjustable for one, more, or all of the neurons in the CNN 3524, such that a reliable output will result from output layer 507. Such adjustments may be performed manually or automatically.

When manually adjusted, the weights are adjusted by the user, sensor logic, etc. in a repeated manner until the output from output layer 507 matches expectations. For example, assume that input layer 503 receives pixel values (color, intensity, shading, etc.) from pixels in a photograph of a giraffe (animal image 506). If the output from output layer 507 includes neuron/node 504, which is associated with "giraffe", then the weights (and/or the algorithms and/or biases in "upstream" nodes/neurons) are adjusted until neuron/node 504 contains the highest value in the output layer 507 when pixel data from a photograph of a giraffe is input into input layer 503.

When automatically adjusted, the weights (and/or algorithms and/or biases) are adjusted using "back propagation", in which weight values and/or biases and/or algorithms of the neurons are adjusted by using a "gradient descent" method that determines which direction each weight value should be adjusted to. This gradient descent process moves the weight in each neuron in a certain direction until the output from output layer 507 improves (e.g., neuron 504 has a higher value than node 506 that is associated with the label "giraffe". However, like the TNN 424 described in FIG. 4, if node 506 has the highest value in the output layer 507 (i.e., CNN 524 "thinks" that the animal image 506 is that of a horse), then there is a defective neuron in the middle layer 505, which is mapped to a particular locus in the patient's brain for identification of which part of the patient's brain is impaired.

Figure 6:
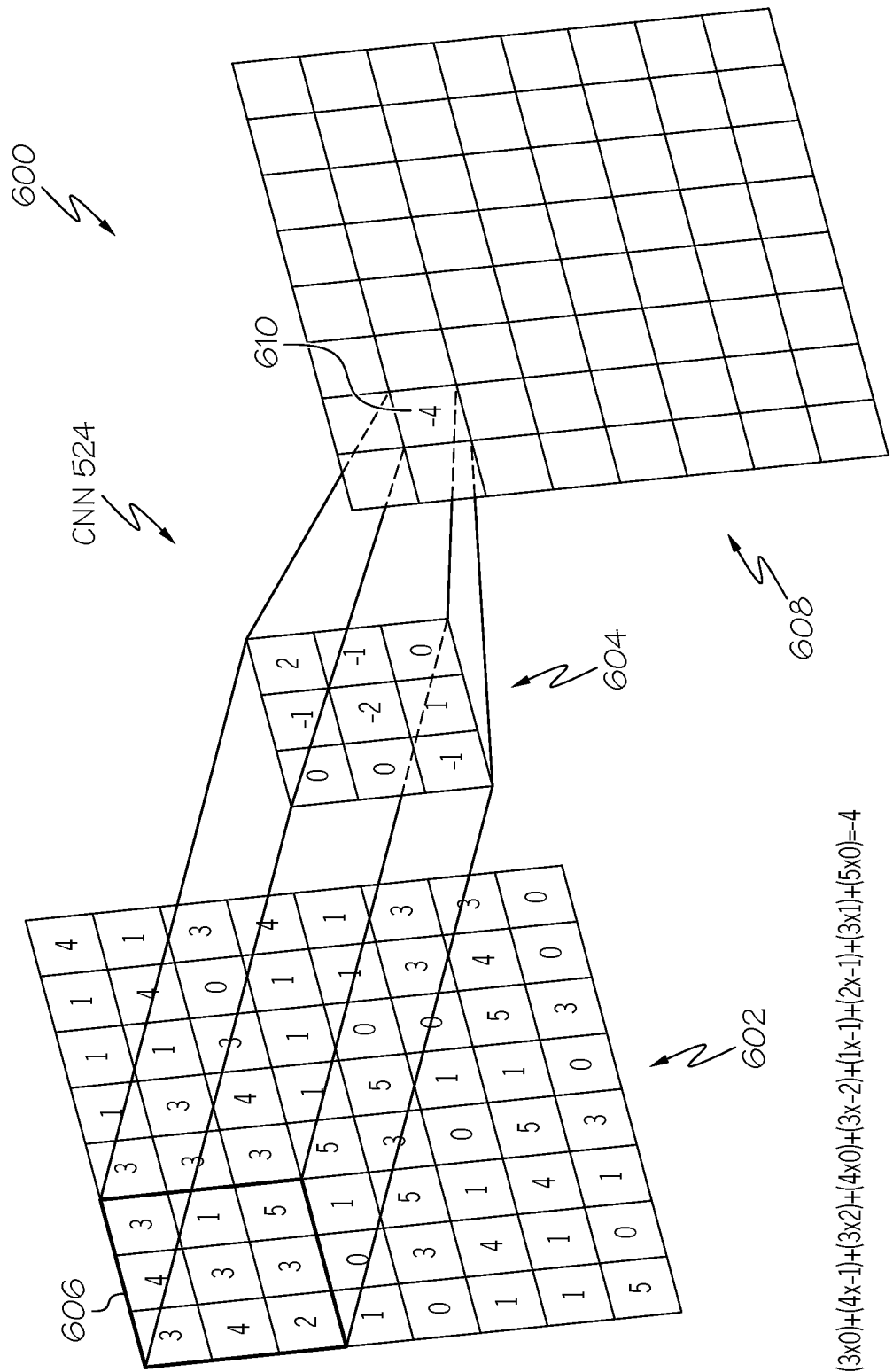
FIG. 6 depicts additional functionality detail of the CNN illustrated in FIG. 5.
Figure 7:
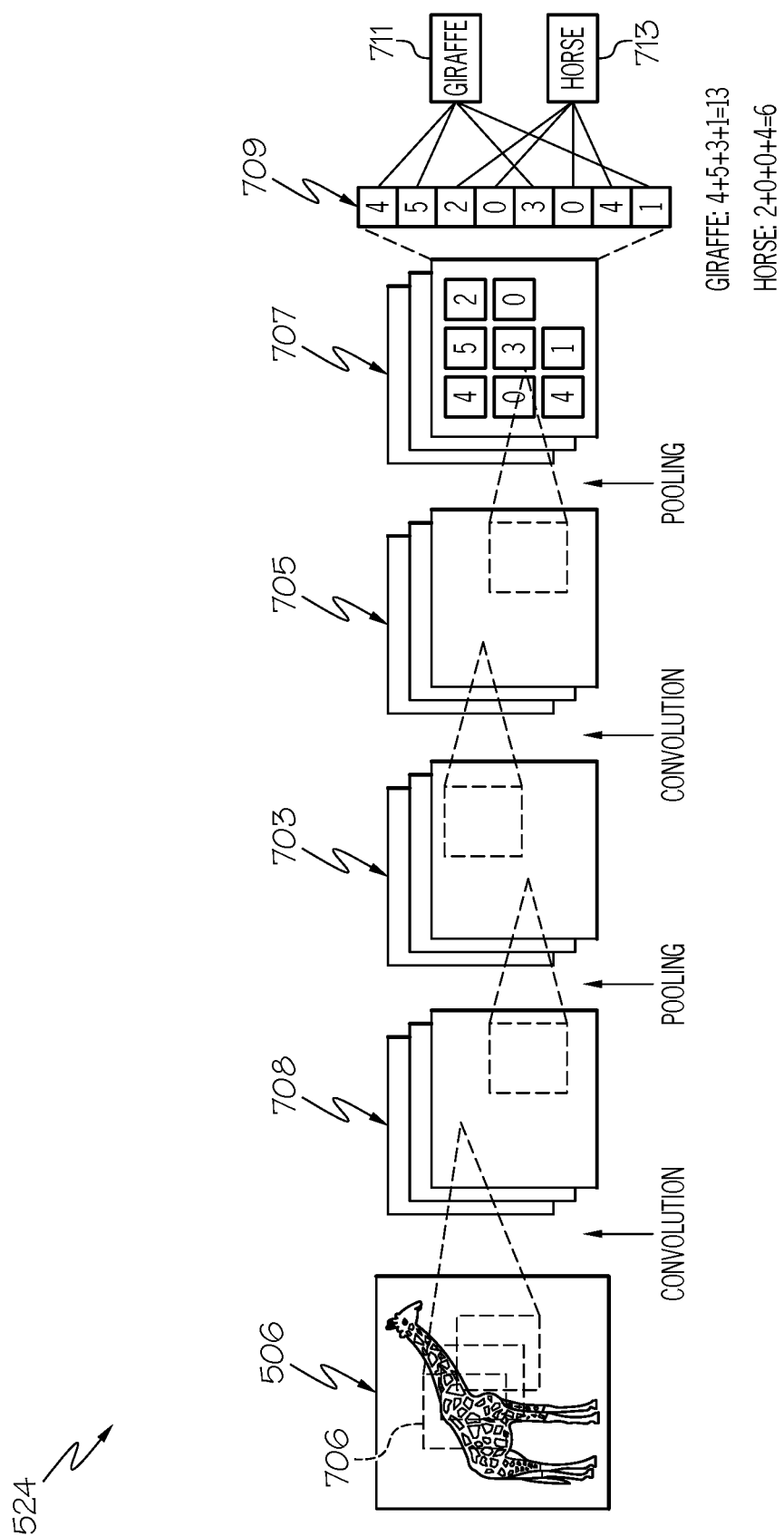
FIG. 7 illustrates an exemplary photo image being evaluated/inferred using a CNN in accordance with one or more other embodiments of the present invention.

A CNN process includes 1) a convolution stage (depicted in FIG. 6), followed by a 2) pooling stage and a classification stage (depicted in FIG. 7).

With reference now to FIG. 6, a convolution/pooling scheme to analyze image data is presented in CNN convolution process 400. As shown in FIG. 6, pixel data from a photographic image (e.g., animal image 506 shown in FIG. 5) populates an input table 602. Each cell in the input table 602 represents a value of a pixel in the photograph. This value is based on the color and intensity for each pixel. A subset of pixels from the input table 602 is associated with a filter 604. That is, filter 604 is matched to a same-sized subset of pixels (e.g., pixel subset 606) by sliding the filter 604 across the input table 602. The filter 604 slides across the input grid at some predefined stride (i.e., one or more pixels). Thus, if the stride is "1", then the filter 604 slides over in increments of one (column) of pixels. In the example shown in FIG. 6, this results in the filter 604 sliding over the subset of pixels shown as pixel subset 606 (3, 4, 3, 4, 3, 1, 2, 3, 5 when read from left to right for each row) followed by filter 604 sliding over the subset of pixels just to the right (4, 3, 3, 3, 1, 3, 2, 5, 3). If the stride were "2", then the next subset of pixels that filter 604 would slide to would be (3, 3, 1, 1, 3, 3, 5, 3, 4).

Filter 604 is applied against each pixel subset using a mathematical formula. That is, the values in the filter 604 are added to, subtracted from, multiplied by, divided by, or otherwise used in a mathematical operation and/or algorithm with the values in each subset of pixels. For example, assume that the values in filter 604 are multiplied against the pixel values shown in pixel subset 606 ((3x0)+(4x−1)+(3x2)+(4x0)+(3x−2)+(1x−1)+(2x−1)+(3x1)+(5x0)) to arrive at the value of −4. This value is then used to populate feature map 608 with the value of −4 in cell 610.

In a preferred embodiment, the convolution step also includes use of an activation function, which transforms the output of the convolution operation into another value. One purpose of the use of an activation function is to create nonlinearity in the CNN. A choice of specific activation function depends on an embodiment. Popular choices of an activation function include a rectified linear unit (ReLU), a leaky ReLU, a sigmoid function, a tanh function, and so on.

In an embodiment, each subset of pixels uses a same filter. However, in a preferred embodiment, the filter used by each subset of pixels is different, thus allowing a finer level of granularity in creating the feature map.

With reference now to FIG. 7, the pooling stage and a classification stage (as well as the convolution stage) of a CNN 524 during inference processing is depicted. That is, once the CNN 524 is optimized by adjusting weights and/or algorithms and/or biases in the neurons (see FIG. 5), by adjusting the stride of movement of the pixel subset 606 (see FIG. 6), and/or by adjusting the filter 604 shown in FIG. 6, then it is able to recognize similar objects in similar photographs.

As shown in FIG. 7, assume that pixels from a photograph (animal image 506) are used as inputs to the input table 602 shown in FIG. 6, using a CNN that has been previously defined and optimized to recognize the image of a giraffe. Assume further that a series of pixel subsets, including the pixel subset 706 (analogous to pixel subset 606 shown in FIG. 6) are convolved (using the process described in FIG. 6), thus resulting in a set of feature maps 708 (analogous to feature map 608 shown in FIG. 6). Once the feature maps 708 are generated, they are pooled into smaller pooled tables 703, in order to reduce the dimensionality of the values, thereby reducing the number of parameters and computations required in the CNN process. Once these pooled tables 703 are created, they themselves are then convoluted to create new (and even more compressed) feature maps 705, which are then pooled to create even more compressed pooled tables 707.

The pooled tables 707 (which in an embodiment is actually a single table) are "unrolled" to form a linear vector, shown in FIG. 7 as a fully connected layer 709. Fully connected layer 509 is connected to prediction output, including prediction output 711 (for a giraffe) and prediction output 713 (for a horse).

For example, assume that for a prediction output to be considered accurate, it must have an arbitrarily chosen total value of 10 or greater for the sum of values from cells in the fully connected layer 709 to which it is connected. As such, the prediction output 711 is connected to cells in the fully connected layer 509 that have the values of 4, 5, 3, and 1, resulting in a sum total of 13. Thus, the CNN 524 concludes that animal image 506 includes an image of a giraffe. In one or more embodiments, an output function, such as a softmax function, amplifies larger output values, attenuates smaller output values, and normalizes all output values in order to ensure that their total sum is one. That is, rather than assigning an arbitrary number (e.g., 10) as being what the sum total of values in certain cells from the connected layer 709 must exceed in order to indicate that a particular entity (e.g., a giraffe) is portrayed in the new photograph, an output function such as a softmax function dynamically adjusts the output values and then normalizes them, such that they sum up to 1.0 or some other predetermined number. Thus, while the described values shown in FIG. 7 describe the concept of output values describing entities in the photographs, in practice a static threshold value is not used in certain embodiments. Rather, in this alternative/preferred embodiment, the system utilizes a normalized summation (as just described), in order to further control the output characteristics, thus more accurately determining the label of the object in the photograph.

The prediction output 713 for a horse is only 6 (2+0+0+4) based on the cells in the fully connected layer 709 to which it is attached. However, if the pixels in the animal image 506 were of a horse, then the fully connected layer 709 (if properly trained) would result in the values of the cells in the fully connected layer 709 that are connected to the prediction output 711 to total less than 10, while the values of the cells in the fully connected layer 709 that are connected to the prediction output 713 would be more than 10.

However, assume now that CNN 524 has created a fully connected layer 708 that gives a total value of 15 (not depicted) in the output cells associated with the predicted output 713 (label "horse"). This indicates that one or more neurons in the CNN 524 are improperly programmed. These improperly programmed neurons have been mapped to specific loci in the patient's brain. Thus, the improperly programmed neurons are used to identify the specific loci in the patient's brain that is impaired (e.g., because of a stroke).

While FIG. 7 depicts that a collection of values from the fully connected layer 709 are used to identify what is in animal image 506, in another embodiment each node/neuron in the fully connected layer 709 is assigned a different label, as depicted in FIG. 4 for a TNN 424.

As discussed above with regard to FIG. 7, inference is the process of using a trained CNN to recognize certain objects from a photograph or other data. In the example in FIG. 7, pixels from animal image 506 are input into a trained CNN (e.g., CNN 524), resulting in the identification and/or labeling of (for display on the photograph/animal image 506) a particular object, such as the giraffe.

That is, a CNN is trained to recognize a certain object (e.g., a giraffe in a photograph). By using a new photograph as an input to the trained CNN, a giraffe in the new photograph is also identified/labeled using a process known as inferencing. This inferencing occurs in real time, and recognizes specific objects (e.g., a giraffe) by running the new photograph through the trained CNN.

Figure 8:
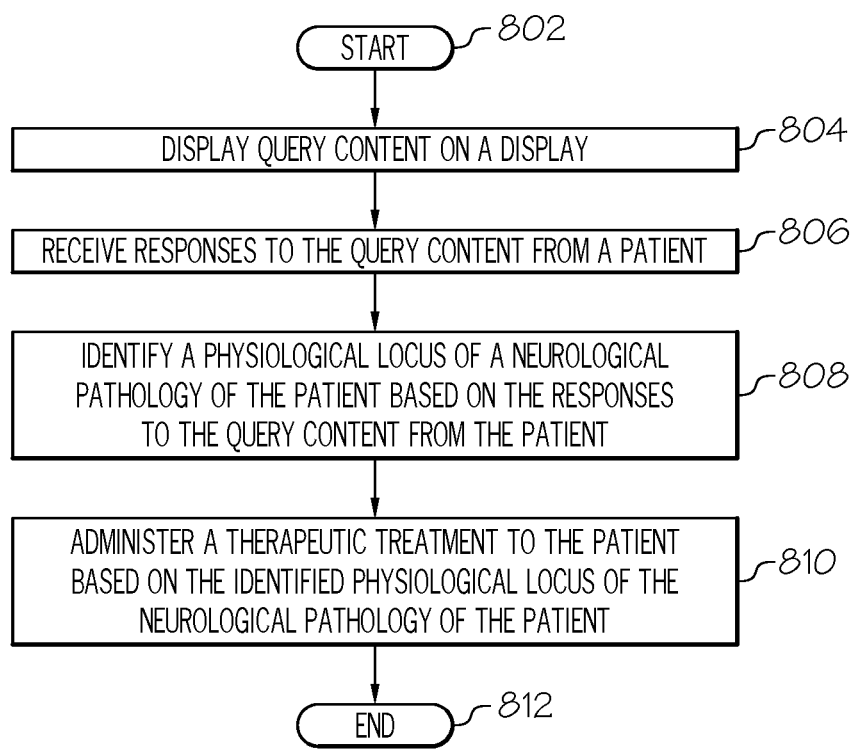
FIG. 8 is a high-level flow chart of one or more steps performed in accordance with one or more embodiments of the present invention.

With reference now to FIG. 8, a high level flow chart of one or more embodiments of the present invention is presented.

After initiator block 802, one or more processors (e.g., processor 104 shown in FIG. 1) displays (e.g., on GUI 202 shown in FIG. 2) query content on a display (e.g., on the patient's computer 152 shown in FIG. 1), as described in block 804. In various embodiments of the present invention, the query content is text content, photographic content, video content, and/or audio-visual content. As such, the "display" is a video screen, a speaker, personal earbuds, etc., depending on the type of content being "displayed" to the patient.

As described in block 806, the processor(s) receive responses to the query content from a patient. That is, the processor(s) function as a conversational agent to receive the inputs from the patient (e.g., from fields 208, 212, 218 shown in FIG. 2).

As described in block 808, the processor(s) identify a physiological locus of a neurological impairment of the patient based on the responses to the query content from the patient. That is, based on how the patient answers the query content, the system determines which part of the brain is affected/impaired. For example, if the part of the brain known by one trained in the field of neuroanatomy as that which processes images is impaired, then the patient will be unable to correctly identify the giraffe in FIG. 2. However, if the part of the brain known to be that which processes text images is impaired, then the patient will be unable to answer a text question such as "What is your best friend's name?"

As described in block 810, a health care provider, the processor(s), the patient's family, and/or the patient himself/herself then administers a therapeutic treatment to the patient based on the identified physiological locus of the neurological impairment of the patient.

The flow-chart ends at terminator block 812.

In an embodiment of the present invention, the therapeutic treatment is a repetitive mental activity that is designed to provide the therapeutic treatment to the patient, and the repetitive mental activity is provided by a template-based conversational agent the communicates with the patient. For example, assume that the patient is unable to remember the name of his/her best friend. As such, the conversational agent repeatedly reminds the patient of the name of his/her best friend (and then directs the patient to enter that name, either immediately or else at a later time) until the patient is able to type in the name with no further hints from the conversational agent (including mnemonic devices, anecdotes designed to trigger the name of the best friend, etc.).

In an embodiment of the present invention, assume again that the therapeutic treatment is a repetitive mental activity that is designed to provide the therapeutic treatment to the patient. As described in FIG. 3, the processor(s) display a graph (e.g., relationship graph 301 shown in GUI 303 in FIG. 3) that includes a representation of a first depicted relationship between the patient (node 305) and a first entity (node 318 in FIG. 3). The processor(s) then determine that the therapeutic treatment has strengthened a recognition of the first depicted relationship between the patient and the first entity. For example, the patient is now able to remember the name of his/her best friend, due to the therapeutic treatment he/she has received.

In response to determining that the therapeutic treatment has strengthened the recognition of the first depicted relationship between the patient and the first entity, the processor(s) adjust an appearance of the first depicted relationship between the patient and the first entity on the graph. For example, the dashed lines from node 305 to box 315 and node 318 switch from being dashed to solid.

In response to determining that the therapeutic treatment has strengthened the recognition of the first depicted relationship between the patient and the first entity, the processor(s) adjust the graph by displaying a second depicted relationship between the patient and a second entity (e.g., the phone number in node 320). The healthcare provider, family, patient, and/or processor(s) then further administer the therapeutic treatment to the patient until recognition of the second depicted relationship between the patient and the second entity has been strengthened (e.g., the patient is not able to remember his/her own phone number).

In an embodiment of the present invention, the therapeutic treatment is a surgical treatment to the physiological locus of the neurological impairment of the patient. That is, once the particular part of the brain that is impaired is identified, it is surgically repaired (e.g., by installing a graft, a stint, etc.).

In an embodiment of the present invention, the therapeutic treatment is a pharmacological treatment of the neurological impairment of the patient. That is, once the particular part of the brain that is impaired is identified, therapeutic medicine is given to the patient to correct the vascular blockage in the brain, etc.

In an embodiment of the present invention, the therapeutic treatment is a repetitive mental activity that is designed to provide the therapeutic treatment to the patient, and the repetitive mental activity is provided by a template-based conversational agent the communicates with the patient. That is, the repetitive mental activity is to repeatedly prompt the patient (with prompts, clues, cues, etc. as long as necessary) to answer a general knowledge or unique knowledge question until the patient's brain has been retrained to remember such knowledge.

In an embodiment of the present invention, one or more processors create an analogous electronic neural network that is analogous to a central nervous system of the patient, and then identify the neurological impairment based on a functionality of the analogous electronic neural network. (See FIGS. 4-7 and associated discussion above.) That is, the neural network model is used to identify what type of cognitive ability (e.g., image recognition, text processing, etc.) is impaired in the patient.

In an embodiment of the present invention, one or more processors create an analogous electronic neural network that is analogous to a central nervous system of the patient, and then identify the physiological locus of the neurological impairment based on a functionality of the analogous electronic neural network. (See FIGS. 4-7 and associated discussion above.) For example, assume that the patient cannot remember the name of his/her best friend. The electronic neural networks depicted in FIGS. 4-7 contain clusters of one or more electronic neurons that are mapped to particular parts of the brain that are involved in human memory (e.g., the hippocampus, the amygdala, the cingulate gyms, the thalamus, the hypothalamus, the epithalamus, the mammillary body, etc.). By identifying which electronic neuron in the electronic neural network is the cause of a faulty output (e.g., the incorrect name "Joe" instead of the correct name "Bob" for the patient's best friend) in the electronic neural network, then the part of the brain that is associated with that electronic neural network is identified as being what is impaired in the patient's physical brain.

Figure 9:
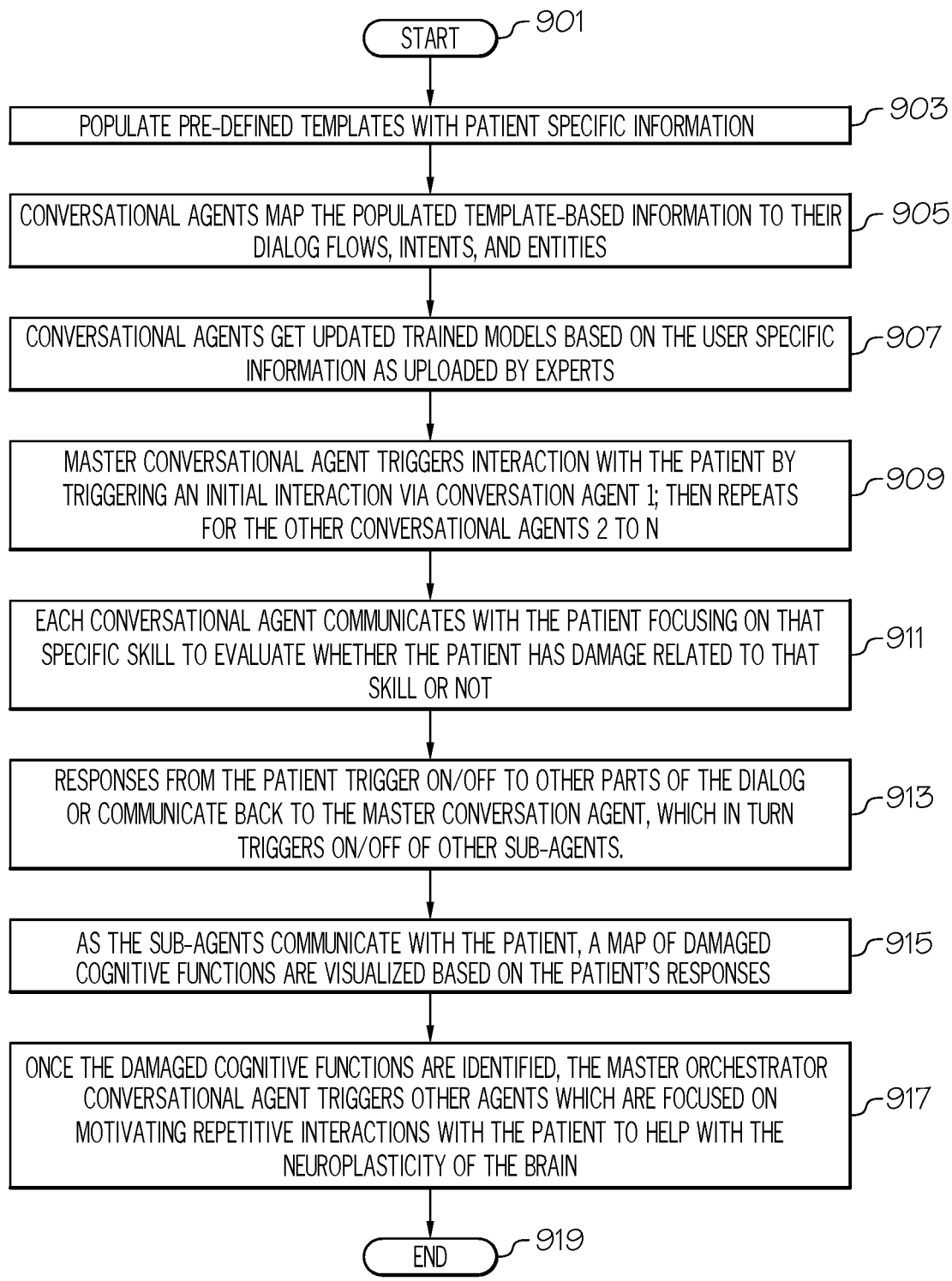
FIG. 9 is another high-level flow chart of one or more steps performed in accordance with one or more embodiments of the present invention.

With reference now to FIG. 9, another high-level flow chart of steps performed in accordance with one or more embodiments of the present invention is presented.

After initiator block 901, doctors, neuropsychologists, family members, friends, and co-workers populate pre-defined templates with information that the patient should know, as described in block 903.

As described in block 905, conversational agents map the populated template-based information (pictures and names of family members, work specific skills, language skills, facial recognition, creative skills, etc.) to their dialog flows, intents, and entities.

As described in block 907, the conversational agents get updated trained models based on the user specific information as uploaded by experts.

As described in block 909, a master conversational agent (e.g., part of NIITL 148 shown in FIG. 1) triggers an interaction with the patient by triggering an initial interaction via conversation agent 1; then repeats for the other conversational agents 2 to N (assuming that each piece and/or type of information that is being "relearned" by the patient has its own conversational agent).

As described in block 911, each conversational agent communicates with the patient, focusing on that specific skill to evaluate whether the patient has damage related to that skill or not.

As described in block 913, responses from the patient trigger ON/OFF to other parts of the dialog or communicate back to the master conversational agent, which in turn triggers ON/OFF of other sub-agents. For example, if a language skills sub-agent determines there is no damage in that part of the brain, that will trigger that there is no reason to invoke the sub-agent focused on facial recognition. In one or more embodiments of the present invention, rules for triggering ON/OFF parts of the dialog are based on rules that are configured by experts before engaging the conversational agent(s).

As described in block 915, as the sub-agents communicate with the patient, a map of damaged cognitive functions is visualized based on the patient's responses. While FIG. 3 shows a very simple example of such a map, in one or more embodiments of the present invention there are scores, hundreds, or even thousands of nodes in the map. These nodes are positioned according to their type, their relationship to the patient, etc. As such, an area of the map that is missing certain clusters of nodes indicates that a particular type of cognitive impairment (e.g., image recognition) has occurred in the patient's brain.

In an embodiment of the present invention, the map is correlated with computed tomography (CT) scans of other patients and/or other maps of other patients to identify commonalities and extract insights across populations. For example, if other patients incorrectly answer some of the questions shown in FIG. 2, just as the current patient did, and it is known that these other patients (who answered the same questions incorrectly) have damage to their hippocampus and/or a certain type of cognitive impairment (e.g., failure to recognize animal shapes), then a presumption is made that the current patient also has damage to his/her hippocampus and/or has this same certain type of cognitive impairment.

As described in block 917, once the damaged cognitive functions are identified, the master orchestrator conversational agent triggers other agents which are focused on motivating repetitive interactions with the patient to help with the neuroplasticity of the brain, in order to ameliorate the damaged/impaired cognitive functions of the patient.

The flow chart ends at terminator block 919.

In one or more embodiments, the present invention is implemented using cloud computing. Nonetheless, it is understood in advance that although this disclosure includes a detailed description on cloud computing, implementation of the teachings recited herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model includes at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but still is able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. In one or more embodiments, it is managed by the organization or a third party and/or exists on-premises or off-premises.

Community cloud: the cloud infrastructure is shared by several organizations and supports a specific community that has shared concerns (e.g., mission, security requirements, policy, and compliance considerations). In one or more embodiments, it is managed by the organizations or a third party and/or exists on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 10:
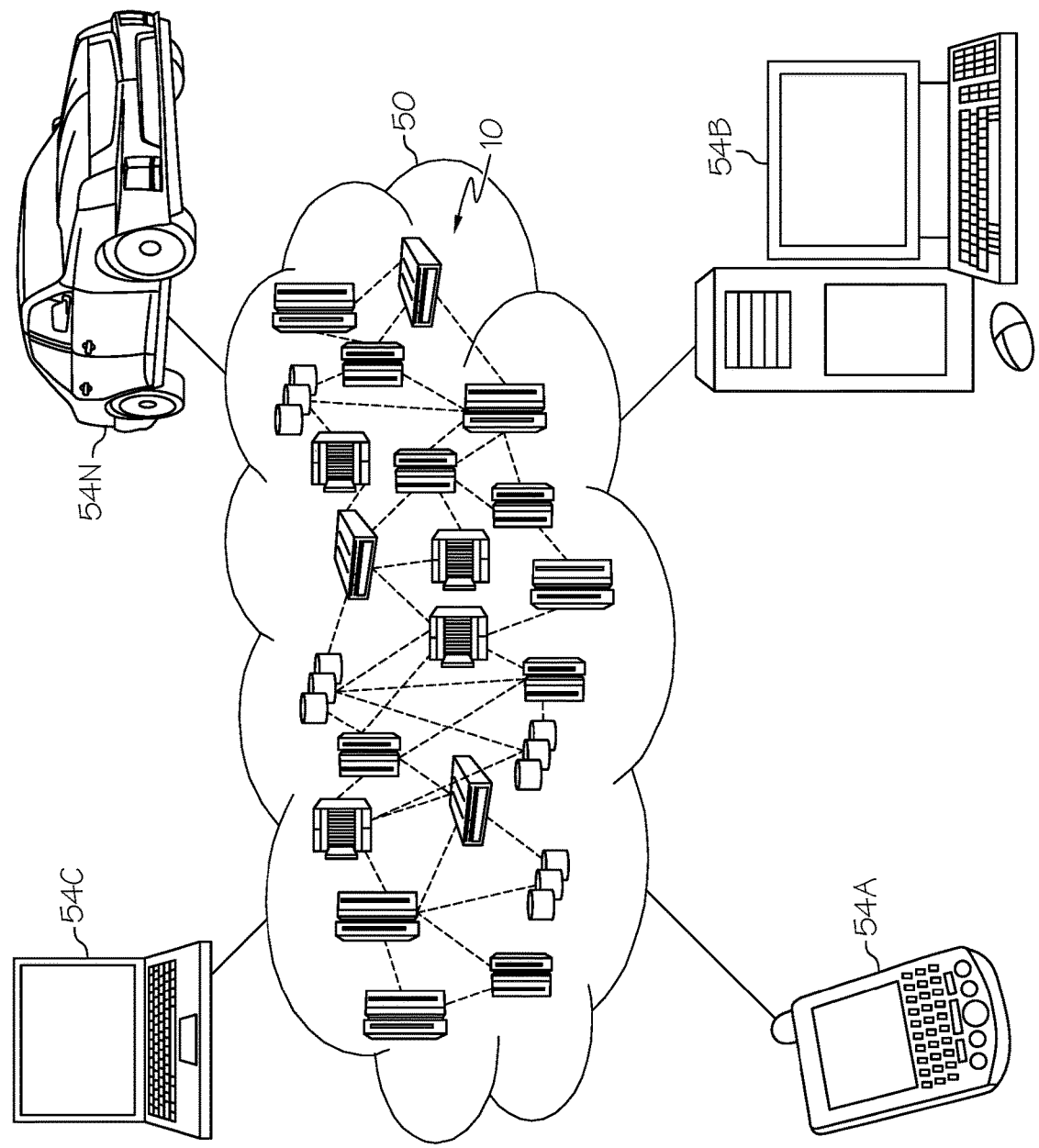
FIG. 10 depicts a cloud computing environment according to an embodiment of the present invention.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N communicate with one another. Furthermore, nodes 10 communicate with one another. In one embodiment, these nodes are grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 10 are intended to be illustrative only and that computing nodes 10 and cloud computing environment 50 can communicate with any type of computerized device over any type of network and/or network addressable connection (e.g., using a web browser).

Figure 11:
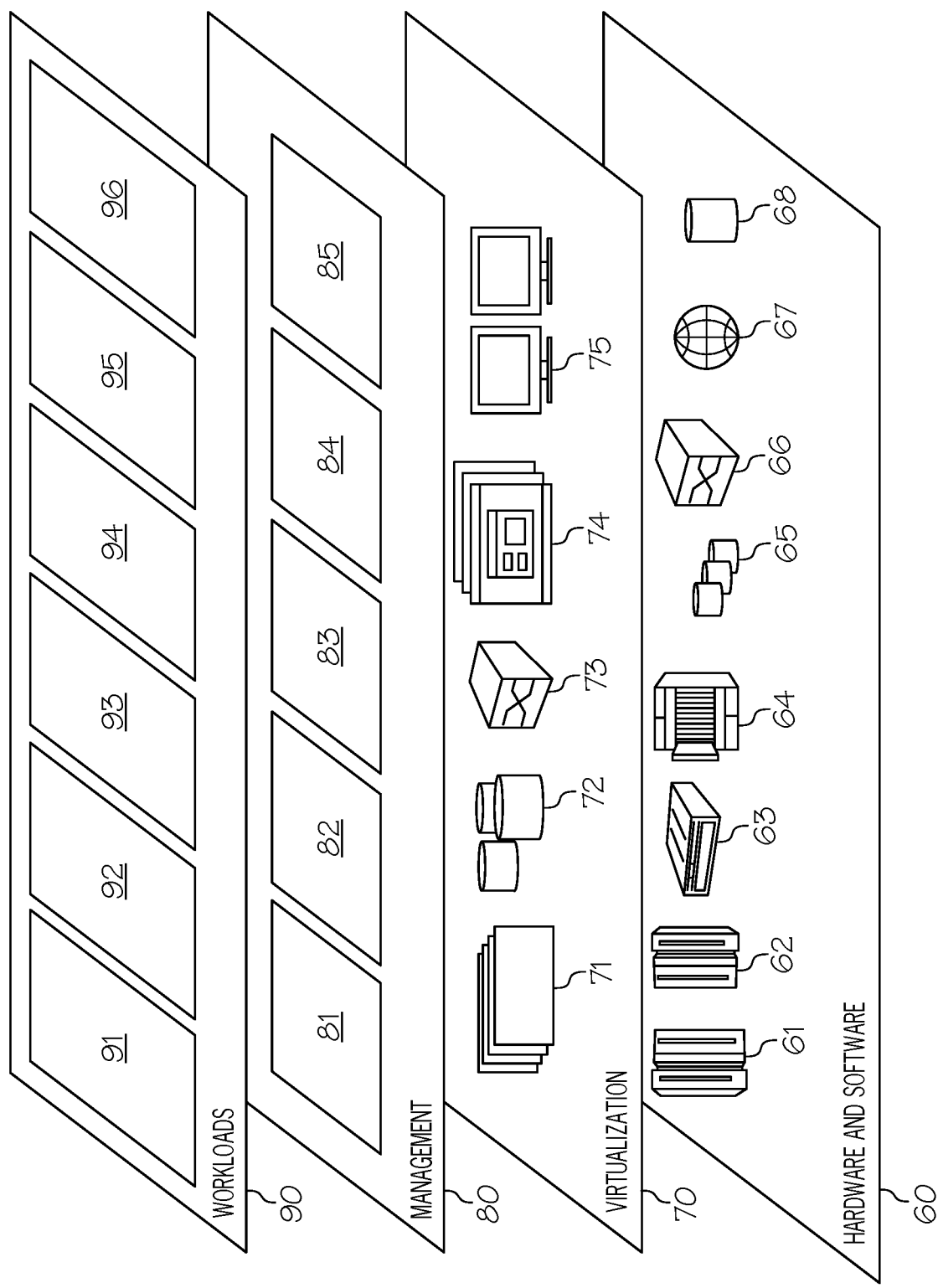
FIG. 11 depicts abstraction model layers of a cloud computer environment according to an embodiment of the present invention.

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities that are provided in one or more embodiments: virtual servers 71; virtual storage 72; virtual networks 73, including virtual private networks; virtual applications and operating systems 74; and virtual clients 75.

In one example, management layer 80 provides the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment are utilized in one or more embodiments. Examples of workloads and functions which are provided from this layer include: mapping and navigation 91; software development and lifecycle management 92; virtual classroom education delivery 93; data analytics processing 94; transaction processing 95; and neurological impairment identification and therapy administering processing 96, which performs one or more of the features of the present invention described herein.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

In one or more embodiments of the present invention, any methods described in the present disclosure are implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, in one or more embodiments of the present invention any software-implemented method described herein is emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A method comprising:
    displaying, by one or more processors, query content on a display;
    receiving, by the one or more processors, responses to the query content from a patient;
    identifying, by the one or more processors, a physiological locus of a neurological impairment of the patient based on the responses to the query content from the patient, wherein the physiological locus of the neurological impairment is a specific area of a central nervous system of the patient;
    creating an analogous electronic neural network that is analogous to a central nervous system of the patient, wherein each component in the analogous electronic neural network performs a function of the specific area of the central nervous system of the patient;
    identifying, by the one or more processors, the neurological impairment based on a functionality of the analogous electronic neural network; and
    administering a therapeutic treatment to the patient based on the identified physiological locus of the neurological impairment of the patient and the identified neurological impairment based on the functionality of the analogous electronic neural network, wherein the therapeutic treatment is a pharmacological treatment of the neurological impairment of the patient, and wherein the pharmacological treatment administers a therapeutic medicine that corrects a vascular blockage in the brain of the patient.

2. The method of claim 1, wherein the therapeutic treatment further comprises a repetitive mental activity that is designed to provide the therapeutic treatment to the patient, and wherein the repetitive mental activity is provided by a template-based conversational agent that communicates with the patient.

3. The method of claim 1, wherein the therapeutic treatment further comprises a repetitive mental activity that is designed to provide the therapeutic treatment to the patient, and wherein method further comprises:
    displaying, by the one or more processors, a graph that comprises a representation of a first depicted relationship between the patient and a first entity;
    determining, by the one or more processors, that the therapeutic treatment has strengthened a recognition of the first depicted relationship between the patient and the first entity;
    in response to determining that the therapeutic treatment has strengthened the recognition of the first depicted relationship between the patient and the first entity, adjusting, by the one or more processors, an appearance of the first depicted relationship between the patient and the first entity on the graph;
    in response to determining that the therapeutic treatment has strengthened the recognition of the first depicted relationship between the patient and the first entity, adjusting, by the one or more processors, the graph by displaying a second depicted relationship between the patient and a second entity; and
    further administering the therapeutic treatment to the patient until a recognition of the second depicted relationship between the patient and the second entity has been strengthened.

4. The method of claim 1, wherein the therapeutic treatment further comprises a surgical treatment to the physiological locus of the neurological impairment of the patient, and wherein the surgical treatment surgically installs a stint in the particular part of the brain of the patient that is impaired.

5. The method of claim 1, and wherein the method further comprises:
    further identifying, by the one or more processors, the physiological locus of the neurological impairment based on a functionality of the analogous electronic neural network.

6. The method of claim 1, wherein the query content comprises general knowledge and unique knowledge, wherein the general knowledge is knowledge that all persons are expected to know, wherein the unique knowledge is knowledge that only the patient is expected to know, and wherein the method further comprises:
    receiving, by the one or more processors, responses to the query content indicating that the patient does not know the general knowledge;
    in response to receiving the responses to the query content indicating that the patient does not know the general knowledge, identifying a first area of the patient's brain that stores general knowledge as being impaired;

receiving, by the one or more processors, responses to the query content indicating that the patient does not know the unique knowledge; and in response to receiving the responses to the query content indicating that the patient does not know the unique knowledge, identifying a second area of the patient's brain that stores unique knowledge as being impaired.

7. The method of claim 2, wherein the repetitive mental activity is a repetitive mental activity that is designed to create an alternative neurological pathway in a brain of the patient, and wherein the alternative neurological pathway performs a neurologically unimpaired activity of the identified physiological locus.

8. A computer program product comprising a computer readable storage medium having program code embodied therewith, wherein the computer readable storage medium is not a transitory signal per se, and wherein the program code is readable and executable by a processor to perform a method comprising:

displaying query content on a display;

receiving responses to the query content from a patient;

identifying a physiological locus of a neurological impairment of the patient based on the responses to the query content from the patient, wherein the physiological locus of the neurological impairment is a specific area of a central nervous system of the patient;

creating an analogous electronic neural network that is analogous to a central nervous system of the patient, wherein each component in the analogous electronic neural network performs a function of a specific area of the central nervous system of the patient;

further identifying the physiological locus of the neurological impairment of the patient based on a functionality of the analogous electronic neural network; and administering a therapeutic treatment to the patient based on the identified physiological locus of the neurological impairment of the patient.

9. The computer program product of claim 8, wherein the therapeutic treatment is a repetitive mental activity that is designed to provide the therapeutic treatment to the patient, and wherein the repetitive mental activity is provided by a template-based conversational agent that communicates with the patient.

10. The computer program product of claim 8, wherein the therapeutic treatment is a repetitive mental activity that is designed to provide the therapeutic treatment to the patient, and wherein method further comprises:

displaying a graph that comprises a representation of a first depicted relationship between the patient and a first entity;

determining that the therapeutic treatment has strengthened a recognition of the first depicted relationship between the patient and the first entity;

in response to determining that the therapeutic treatment has strengthened the recognition of the first depicted relationship between the patient and the first entity, adjusting an appearance of the first depicted relationship between the patient and the first entity on the graph;

in response to determining that the therapeutic treatment has strengthened the recognition of the first depicted relationship between the patient and the first entity, adjusting the graph by displaying a second depicted relationship between the patient and a second entity; and further administering the therapeutic treatment to the patient until a recognition of the second depicted relationship between the patient and the second entity has been strengthened.

11. The computer program product of claim 8, wherein the therapeutic treatment is a surgical treatment to the physiological locus of the neurological impairment of the patient.

12. The computer program product of claim 8, wherein the therapeutic treatment is a pharmacological treatment of the neurological impairment of the patient, and wherein the pharmacological treatment administers a therapeutic medicine that corrects a vascular blockage in the brain of the patient.

13. The method of claim 1, wherein the physiological locus of the neurological impairment is from a set of physiological loci of neurological impairments in a human brain, where the set consists of a first physiological locus and a second physiological locus, wherein the first physiological locus processes visual images of objects, and wherein the second physiological locus processes text images of language text.

14. The computer program product of claim 8, wherein the program instructions are provided as a service in a cloud environment.

15. A computer system comprising one or more processors, one or more computer readable memories, and one or more computer readable non-transitory storage mediums, and program instructions stored on at least one of the one or more computer readable non-transitory storage mediums for execution by at least one of the one or more processors via at least one of the one or more computer readable memories, the stored program instructions executed to perform a method comprising:

displaying query content on a display;

receiving responses to the query content from a patient;

identifying a physiological locus of a neurological impairment of the patient based on the responses to the query content from the patient, wherein the physiological locus of the neurological impairment is a specific area of a central nervous system of the patient;

creating an analogous electronic neural network that is analogous to a central nervous system of the patient, wherein each component in the analogous electronic neural network performs a function of a specific area of the central nervous system of the patient; and further identifying the physiological locus of the neurological impairment of the patient based on a functionality of the analogous electronic neural network; and administering a therapeutic treatment to the patient based on the identified physiological locus of the neurological impairment of the patient.

16. The computer system of claim 15, wherein the therapeutic treatment is a repetitive mental activity that is designed to provide the therapeutic treatment to the patient, and wherein the repetitive mental activity is provided by a template-based conversational agent the communicates with the patient.

17. The computer system of claim 15, wherein the therapeutic treatment is a repetitive mental activity that is designed to provide the therapeutic treatment to the patient, and wherein method further comprises:

displaying a graph that comprises a representation of a first depicted relationship between the patient and a first entity;

determining that the therapeutic treatment has strengthened a recognition of the first depicted relationship between the patient and the first entity;

in response to determining that the therapeutic treatment has strengthened the recognition of the first depicted relationship between the patient and the first entity, adjusting an appearance of the first depicted relationship between the patient and the first entity on the graph;

in response to determining that the therapeutic treatment has strengthened the recognition of the first depicted relationship between the patient and the first entity, adjusting the graph by displaying a second depicted relationship between the patient and a second entity; and further administering the therapeutic treatment to the patient until a recognition of the second depicted relationship between the patient and the second entity has been strengthened.

18. The computer system of claim 15, wherein the program instructions are provided as a service in a cloud environment.

* * * * *